United States Patent [19]

Eckhardt et al.

[11] 4,150,144
[45] Apr. 17, 1979

[54] 3-PHENYL-OXAZOLIDINE-2,4-DIONE MICROBICIDES

[75] Inventors: Wolfgang Eckhardt, Lörrach, Fed. Rep. of Germany; Walter Kunz, Oberwil, Switzerland

[73] Assignee: Ciba-Geigy Corporation, Ardsley, N.Y.

[21] Appl. No.: 876,781

[22] Filed: Feb. 10, 1978

[30] Foreign Application Priority Data

Feb. 15, 1977 [CH] Switzerland ............. 1845/77

[51] Int. Cl.² ............. C07D 263/44; A01N 9/28
[52] U.S. Cl. .................... 424/272; 260/307 B
[58] Field of Search ............. 260/307 B; 424/272

[56] References Cited

U.S. PATENT DOCUMENTS

| | | | |
|---|---|---|---|
| 3,703,526 | 11/1972 | Sato et al. | 260/307 B |
| 3,966,750 | 6/1976 | Mangold et al. | 260/307 B |
| 3,995,049 | 11/1976 | Mangold et al. | 424/272 |

FOREIGN PATENT DOCUMENTS

| | | |
|---|---|---|
| 1269636 | 1963 | France. |
| 1284516 | 1963 | France. |

OTHER PUBLICATIONS

Baranov et al. Khim.–Farmasevt. Zh. 1970, (3), 25–28.

*Primary Examiner*—Raymond V. Rush
*Attorney, Agent, or Firm*—Harry Falber

[57] ABSTRACT

3-Phenyl-oxazolidine-2,4-dione derivatives can be halogenated directly, without splitting of the heterocyclic ring. The products thus obtained have a fungicidal action which is substantially wider than that of compounds hitherto known.

9 Claims, No Drawings

3-PHENYL-OXAZOLIDINE-2,4-DIONE MICROBICIDES

The invention relates to novel 3-phenyl-oxazolidin-2,4-diones, to a process for producing them, to microbicidal compositions which contain these compounds as active substances, and to a process for combating fungi and bacteria, especially phytopathogenic fungi.

The novel compounds correspond to the formula I

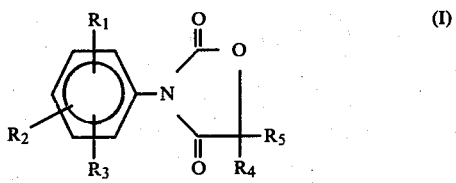

wherein
$R_1$ represents fluorine, chlorine, or bromine,
$R_2$ and $R_3$ independently of one another represent hydrogen, chlorine or bromine,
$R_4$ represents methyl or ethyl, and
$R_5$ represents chlorine, bromine or iodine.

There are known a number of compounds which are structurally related to the oxazolidine-diones of the general formula I. From the German Offenlegungsschrift No. 1,811,843 are known, for example, 3-(3,5-dichlorophenyl)-oxazolidine-2,4-diones as plant fungicides for combating in particular Botrytis. Further 'Botrytis agents' from this class of substances are suggested in the German Offenlegungsschrift No. 2,207,576.

It has now been shown that, surprisingly, compounds of the general formula I have, compared with the known oxazolidine-diones a novel and very favorable sphere of action, also against other pathogens causing plant diseases.

Fungi occurring on plants or on parts of plants (fruit, blossom, foliage, stalks, tubers or roots) can be inhibited or destroyed by application of the active substances of the formula I, and also parts of plants subsequently growing remain protected from such fungi. The compounds of the formula I also have a preventive action. They are effective, for example, against the phytopathogenic fungi belonging to the following classes: Ascomycetes (e.g., Erysiphaceae); Basidiomycetes such as, in particular, rust fungi (Puccinia, Hemileia, etc.); Fungi imperfecti (e.g., Botrytis and Cercospora) or Phycomycetes (e.g., Oomycetes such as Plasmopara). The compounds of the formula I can also be used as dressing agents for the treatment of seed (fruit, tubers and grain) and plant cuttings to preserve them from fungus infections, and also against phytopathogenic fungi occurring in the soil. Examples of cultivated plants to be protected are: cereals, maize, rice, vegetables, sugar beet, soya beans, peanuts, fruit trees, ornamental plants, grape vines, hops and cucurbitaceae (cucumbers, pumpkins and melons), also potatoes, tobacco and tomatoes, as well as banana, cocoa and natural rubber plants.

Compounds of the formula I are also technically important intermediates; the exchange of a halogen atom $R_5$ (chlorine, bromine or iodine) for another radical leads to further valuable fungicides.

The compounds of the formula I can be produced, in accordance with the following reaction pattern, from compounds of the formula II by halogenation, with $R_1$ to $R_4$ having the meanings given for the formula I:

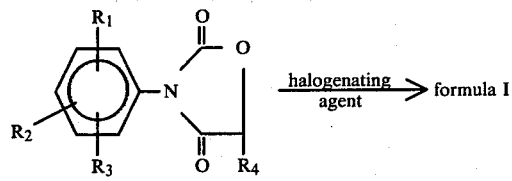

The halogenating agents used can be sulphuryl halides, e.g., $SO_2Br_2$, $SO_2Cl_2$, elementary halogen or N-haloimides, such as N-bromosuccinimide. Halogenation with, for example, elementary halogen is preferably performed in the presence of radical-formers. Examples of these are light (h·ν) and others such as peroxides (dibenzoyl peroxide), α,α'-azoisobutyronitrile or trichlorobromomethane. By elementary halogen is meant primarily chlorine or bromine.

The introduction of a substituent $R_5$=iodine is effected preferably by firstly bromination of a product of the formula II, and subsequent exchange of the introduced bromine atom for iodine with the aid of alkali iodide.

The reaction temperatures are between 0° and 120° C., preferably between 50° and 100° C.

Solvents which can be used are inert aliphatic hydrocarbons such as petroleum ether, benzene or toluene, preferably however halogenated hydrocarbons, e.g., methylene chloride, ethylene chloride, chloroform or carbon tetrachloride, and also anhydrous acetic acid, all suitable for halogenation.

This reaction, characterized by high yields, is surprising. The smooth halogenation of compounds of the formula II, occurring without splitting of the heterocyclic ring, was not to be anticipated.

Some compounds of the formula II are known, for example the production of 3-(3,5-dichlorophenyl)-5-methyl-oxazolidine-2,4-dione by reaction of 3,5-dichlorophenyl-isocyanate and isopropyl lactate and the corresponding production of 3-(3,5-dichlorophenyl)-5-ethyloxazolidine-2,4-dione from propyl α-hydroxybutyrate are described in the German Offenlegungsschrift No. 1,811,843. By suitable choice of the substituted phenylisocyanates to be used, it is possible to produce in an analogous manner also the other compounds of the formula II.

Compounds of the formulae I and II have in the 5-position of the heterocyclic ring an optically active center, and can accordingly be resolved into antipodes. Such antipodes can also be specifically produced by suitable choice of the starting materials, e.g., by use selectively of L(−)-lactate or D(+)-lactate (or by use of one of the two optical antipodes of an α-hydroxybutyrate) and subsequent halogenation, according to the invention, of the compounds of the formula II thus obtained. The optical isomers of the compounds of the formula I have a differing microbicidal action.

The subgroup of the formula I preferred as microbicides is derived from 3,5-dichloroaniline. Among these are the preferred compounds
3-(3,5-dichlorophenyl)-5-bromo-5-methyl-oxazolidine-2,4-dione and
3-(3,5-dichlorophenyl)-5-iodo-5-methyl-oxazolidine-2,4-dione.

The production of compounds of the formula I is illustrated in the examples 1 and 2. Further examples of compounds according to the invention are given in the Table which follows. The temperature values are expressed in degrees centigrade.

EXAMPLE 1

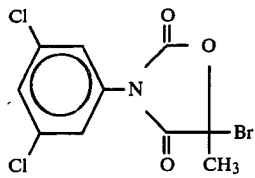

3-(3,5-Dichlorophenyl)-5-bromo-5-methyl-oxazolidine-2,4-dione (compound No. 2)

13 g of the 3-(3,5-dichlorophenyl)-5-methyl-oxazolidine-2,4-dione, produced with ring closure by reaction of 3,5-dichlorophenylisocyanate and L(—)-lactate, and 10.7 g of N-bromosuccinimide are taken up in 180 ml of carbon tetrachloride. The reaction mixture is then irradiated with a 100 W bulb, in consequence of which the reaction mixture commences to boil. There is then added a spatula tip of α,α'-azoisobutyronitrile, and stirring is thus maintained for 8 hours at boiling temperature. After cooling, the solvent is distilled off, and the residue is stirred in 500 ml of warm water (50°–55° C.) for 3 hours. The undissolved final product is filtered off, and subsequently well washed with water at 55°. After drying, there remains 16.7 g (98.5% of theory) of final product, m.p. 154°–156°.

EXAMPLE 2

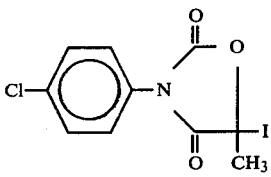

3-(4-Chlorophenyl)-5-iodo-5-methyl-oxazolidine-2,4-dione (compound No. 48)

6.1 g (0.02 mole) of the 3-(4-chlorophenyl)-5-bromo-5-methyl-oxazolidine-2,4-dione, produced in a manner analogous to that described in Example 1, and 33.2 g (0.2 mole) of potassium iodide are placed, together with a spatula tip of benzyltriethylammonium chloride, in 50 ml of water, and the mixture is stirred at 50° for 7 days. It is then cooled to room temperature, and the solid product is filtered off with suction. After washing with water, the crude product is taken up in methylene chloride, and extracted once with water. The organic phase is then dried over sodium sulphate, filtered, and concentrated in a vacuum evaporator. The substance remaining behind is digested with a small amount of ether/petroleum ether, then filtered off with suction and dried. There is obtained a yield of 3.3 g of substance having a melting point of 132°–142°.

The following compounds of the formula I are produced in an analogous manner:

| Comp. No. | $R_1$ | $R_2$ | $R_3$ | $R_4$ | $R_5$ | Physical constants |
|---|---|---|---|---|---|---|
| 1 | 3-Cl | H | 5-Cl | $CH_3$ | Cl | m.p. 58°–160° |
| 2 | 3-Cl | H | 5-Cl | $CH_3$ | Br | m.p. 154°–156° |
| 3 | 3-Cl | H | 5-Cl | $C_2H_5$ | Cl | m.p. 163°–166° |
| 4 | 3-Cl | H | 5-Cl | $C_2H_5$ | Br | m.p. 158°–162° |
| 5 | 3-Cl | 4-Cl | H | $CH_3$ | Cl | m.p. 133°–134° |
| 6 | 3-Cl | 4-Cl | H | $CH_3$ | Br | m.p. 135°–137° |
| 7 | 3-Cl | 4-Cl | H | $C_2H_5$ | Cl | m.p. 136°–138° |
| 8 | 3-Cl | 4-Cl | H | $C_2H_5$ | Br | m.p. 134°–137° |
| 9 | 2-Cl | H | H | $CH_3$ | Br | |
| 10 | 2-Cl | H | 5-Cl | $CH_3$ | Cl | m.p. 130°–142° |
| 11 | 2-Cl | H | 5-Cl | $CH_3$ | Br | m.p. 136°–140° |
| 12 | 2-Br | H | H | $C_2H_5$ | Cl | m.p. 78°–80° |
| 13 | 3-Br | H | H | $CH_3$ | Cl | m.p. 100°–104° |
| 14 | 4-Br | H | H | $CH_3$ | Br | m.p. 137°–139° |
| 15 | 4-F | H | H | $CH_3$ | Br | m.p. 114°–116° |
| 16 | 4-F | H | H | $CH_3$ | Cl | m.p. 105°–111° |
| 17 | 4-Cl | H | H | $CH_3$ | Br | m.p. 125°–127° |
| 18 | 2-Cl | 4-Cl | 5-Cl | $CH_3$ | Cl | m.p. 109°–113° |
| 19 | 2-Cl | 4-Cl | 5-Cl | $CH_3$ | Br | m.p. 106°–110° |
| 20 | 3-Cl | 4-F | H | $CH_3$ | Br | m.p. 130°–135° |
| 21 | 3-Cl | 4-F | H | $C_2H_5$ | Cl | m.p. 138°–142° |
| 22 | 3-Cl | H | H | $CH_3$ | Br | m.p. 97°–100° |
| 23 | 3-Cl | H | H | $CH_3$ | Cl | $n_D^{22}$ 1.5647 |
| 24 | 2-Cl | H | 4-Cl | $CH_3$ | Br | m.p. 120°–124° |
| 25 | 2-Cl | H | 6-Cl | $CH_3$ | Br | m.p. 89°–95° |
| 26 | 2-Cl | H | 4-Cl | $C_2H_5$ | Cl | |
| 27 | 2-Cl | 3-Cl | H | $CH_3$ | Br | m.p. 101°–105° |
| 28 | 2-Br | H | 4-Br | $CH_3$ | Br | m.p. 126°–129° |
| 29 | 2-F | H | H | $CH_3$ | Br | |
| 30 | 3-F | H | H | $CH_3$ | Cl | |
| 31 | 2-Cl | 4-Cl | 6-Cl | $CH_3$ | Br | |
| 32 | 2-Cl | 4-Cl | 6-Cl | $CH_3$ | Cl | |
| 33 | 4-Cl | H | H | $CH_3$ | Cl | m.p. 116°–118° |
| 34 | 3-Br | H | H | $CH_3$ | Br | m.p. 114°–117° |
| 35 | 4-Br | H | H | $CH_3$ | Cl | m.p. 128°–130° |
| 36 | 2-Br | H | H | $CH_3$ | Cl | m.p. 71°–75° |
| 37 | 2-Br | H | H | $CH_3$ | Br | m.p. 67°–72° |
| 38 | 2-Cl | 4-Cl | H | $CH_3$ | Cl | |
| 39 | 2-Cl | 6-Cl | H | $CH_3$ | Cl | |
| 40 | 2-Cl | 3-Cl | H | $CH_3$ | Cl | m.p. 106°–108° |
| 41 | 3-Cl | 4-F | H | $CH_3$ | Cl | m.p. 134°–136° |
| 42 | 3-Cl | 5-Cl | H | $CH_3$ | I | m.p. 148°–152° |
| 43 | 3-Cl | 4-Cl | H | $CH_3$ | I | m.p. 137°–140° |
| 44 | 3-Cl | 4-F | H | $CH_3$ | I | m.p. 126°–129° |
| 45 | 2-Cl | 4-Cl | 5-Cl | $CH_3$ | I | m.p. 102°–105° |
| 46 | 2-Cl | 5-Cl | H | $CH_3$ | I | m.p. 133°–136° |
| 47 | 3-Cl | H | H | $CH_3$ | I | m.p. 105°–109° |
| 48 | 4-Cl | H | H | $CH_3$ | I | m.p. 132°–142° |
| 49 | 3-Cl | 5-Cl | H | $C_2H_5$ | I | m.p. 164°–160° |

In order to broaden the biological sphere of action desired in practice, the active substances of the formula I can be used together with further fungicides, bactericides, herbicides, insecticides, acaricides, nematocides and/or rodenticides, as well as with fertilisers and other plant nutrients, or with agents regulating plant growth.

The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilizers.

The content of active substance in commercial compositions is between 0.1 and 90%.

For application, the compounds of the formula I can be in the following forms (the weight-percentage figures in brackets signify advantageous amounts of active substance):

solid preparations:
dusts and scattering agents (up to 10%), granulates [coated granules, impregnated granules and homogeneous granules] or pellets (1 to 80%);

liquid preparations:
(a) water-dispersible concentrates of active substance: wettable powders and pastes (25 to 90% in the commercial packing, 0.01 to 15% in ready-for-use solutions); emulsion concentrates and solution concentrates 10 to 50%, 0.01 to 15% in ready-for-use solutions);

(b) solutions (0.1 to 20%); aerosols.

The active substances of the formula I of the present invention can be formulated for example as follows.

Dust:
The following substances are used to produce (a) a 5% dust and (b) a 2% dust:
5 parts of active substance,
95 parts of talcum;
(b) 2 parts of active substance,
1 part of highly dispersed silicic acid, and
97 parts of talcum.

The active substances are mixed and ground with the carriers, and in this form they can be applied by dusting.

Granulate:
The following substances are used to produce a 5% granulate:
5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone; the polyethylene glycol and cetyl polyglycol ether are then added. The solution thus obtained is sprayed onto kaolin, and the acetone is subsequently evaporated off in vacuo. A microgranulate of this kind is advantageously used for combating soil fungi.

Wettable powder:
The following constituents are used to produce (a) a 70% wettable powder, (b) a 40% wettable powder, (c) and (d) a 25% wettable powder, and (e) a 10% wettable powder:
(a) 70 parts of active substance,
5 parts of sodium dibutylnaphthylsulphonate,
3 parts of naphthalenesulphonic acid/phenolsulphonic acid/formaldehyde condensate 3:2:1,
10 parts of kaolin, and
12 parts of Champagne chalk;
(b) 40 parts of active substance,
5 parts of sodium lignin sulphonate,
1 part of sodium dibutylnaphthalenesulphonate, and
54 parts of silicic acid;
(c) 25 parts of active substance,
4.5 parts of calcium lignin sulphonate,
1.9 parts of Champagne chalk/hydroxyethylcellulose mixture (1:1),
1.5 parts of sodium dibutylnaphthalenesulphonate,
19.5 parts of silicic acid,
19.5 parts of Champagne chalk, and
28.1 parts of kaolin;
(d) 25 parts of active substance,
2.5 parts of isooctylphenoxy-polyoxyethylene-ethanol,
1.7 parts of Champagne chalk/hydroxyethylcellulose mixture (1:1),
8.3 parts of sodium aluminium silicate,
16.5 parts of kieselguhr, and
46 parts of kaolin; and
(e) 10 parts of active substance,
3 parts of a mixture of the sodium salts of saturated fatty alcohol sulphates,
5 parts of naphthalenesulphonic acid/formaldehyde condensate, and
82 parts of kaolin.

The active substances are intimately mixed in suitable mixers with the additives, and the mixture is then ground in the appropriate mills and rollers. There are obtained wettable powders which have excellent wetting and suspension properties, which can be diluted with water to give suspensions of the desired concentration, and which can be used in particular for leaf application.

Emulsifiable concentrate:
The following substances are used to produce a 25% emulsifiable concentrate:
25 parts of active substance,
2.5 parts of epoxidised vegetable oil,
10 parts of an alkylarylsulphonate/fatty alcohol polyglycol ether mixture,
5 parts of dimethylformamide, and
57.5 parts of xylene.

Emulsions of the desired concentration can be prepared from these concentrates by dilution with water; and these emulsions are particularly suitable for leaf application.

EXAMPLE 3

Action against *Cercospora personata* (=C. arachidicola) on peanut plants

Three-week-old peanut plants were sprayed with a spray liquor produced from wettable powder of the active substance (0.02% of active substance). After about 12 hours, the treated plants were dusted with a conidiospore suspension of the fungus. The infested plants were then incubated for about 24 hours at >90% relative humidity, and subsequently placed in a greenhouse at about 22° C. The fungus infestation was assessed after 12 days.

Compared with the untreated control plants, the plants which had been treated with the active substances of the formula I showed only slight fungus infestation or none at all, for example compound No. 16. Fungus infestation was completely prevented with the compounds Nos. 2 and 42.

EXAMPLE 4

Action against *Botrytis cinerea* on beans
(Residual-protective action)

Bean plants about 10 cm in height were sprayed with a spray liquor produced from wettable powder of the active substance (0.02% of active substance). After 48 hours, the plants were infested with a conidiospore suspension of the fungus. The infested plants were incubated for 3 days at 95–100% relative humidity at 21° C., and the fungus infestation was then assessed. The compounds Nos. 1, 2 and 42 prevented fungus infestation completely.

EXAMPLE 5

Action against *Puccinia graminis* f. sp. secalis on rye plants

Residual-protective action

Rye plants were sprayed, 4 days after sowing, with a spray liquor prepared from wettable powder of the active substance (0.06% of active substance). After 24 hours, the treated plants were infested with a uredospore suspension of the fungus. After an incubation time of 48 hours at 95–100% relative humidity at about 20° C., the infested plants were placed in a greenhouse at about 22° C. The assessment of the extent of the occurring rust pustules was made 12 days after infestation. Compared with the infestation by rust fungus on the untreated but infested control plants, that on the plants treated with compounds of the formula I was greatly reduced or completely prevented. The compounds Nos. 2, 5, 6, 11, 14, 19, 23, 24, 33 and 42 prevented fungus infestation either completely or almost completely (0–10% infestation).

EXAMPLE 6

Action against *Plasmopara viticola* (Bert. et Curt.) (Berl. et DeToni) on grape vines Residual preventive action Grape-vine cuttings of the "Chasselas" variety were grown in a greenhouse. Three plants in the 10-leaf stage were sprayed with a spray liquor produced from active substance formulated as wettable powder (0.06% of active substance). After drying of the sprayed-on coating, the plants were uniformly infested, on the under side, with the spore suspension of the fungus. The plants were subsequently kept for 8 days in a moist chamber. Disease symptoms were clearly visible on the control plants after this period of time. Size and number of the areas of infestation on the treated plants served as a criterion for the evaluation of effectiveness.

Compounds of the formula I produced a high reduction of fungus infestation to 0–20%. The compounds Nos. 2 and 42 prevented fungus infestation completely.

EXAMPLE 7

Action against *Hemileia vastatrix* on *Coffea arabica*

Residual-protective action

Coffee plants about 15 cm in height were sprayed with a spray liquor produced from wettable powder of the active substance. (0.06%). After 24 hours, the treated plants were infested with a spore suspension of rust fungus. The infested coffee plants were placed for 48 hours in a moist chamber, and subsequently in a greenhouse until the outbreak of rust pustules occurred (about 4 weeks). The reduction in the number of rust pustules was taken as a criterion of assessment for the test substances. Compounds of the formula I displayed a strong fungicidal action; the compounds Nos. 2 and 42 did this even at a concentration in the spray liquor of only 0.02%.

EXAMPLE 8

Action against *Venturia inaequalis* on apple shoots

Residual-protective action

Apple cuttings having new shoots 10–20 cm long were sprayed with a spray liquor of the active substance (0.06% of active substance). After 24 hours, the treated plants were infested with a conidiospore suspension of the fungus. The plants were then incubated for 5 days at 90–100% relative humidity, and subsequently kept for a further 10 days in a greenhouse at 20°–24° C. The amount of scab formed was assessed 15 days after infestation of the plants. The compounds Nos. 5 and 33 and also others prevented fungus infestation completely.

We claim:

1. A compound corresponding to the formula

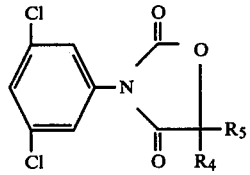

wherein $R_4$ is methyl or ethyl and $R_5$ is chlorine, bromine or iodine.

2. 3-(3,5-Dichlorophenyl)-5-bromo-5-methyl-oxazolidine-2,4-dione according to claim 1.

3. 3-(3,5-Dichlorophenyl)-5-iodo-5-methyl-oxazolidine-2,4-dione according to claim 1.

4. A microbicidal composition comprising a microbicidally effective amount of a compound according to claim 1, together with a suitable carrier therefor.

5. The microbicidal composition of claim 4, wherein said compound is 3-(3,5-dichlorophenyl)-5-bromo-5-methyl-oxazolidine-2,4-dione.

6. The microbicidal composition of claim 4, wherein said compound is 3-(3,5-dichlorophenyl)-5-iodo-5-methyl-oxazolidine-2,4-dione.

7. A method of controlling phytopathogenic fungi or of preventing attack by said fungi comprising applying to plants or parts of plants a fungicidally effective amount of a compound according to claim 1.

8. The method of claim 7, wherein said compound is 3-(3,5-dichlorophenyl)-5-bromo-5-methyl-oxazolidine-2,4-dione.

9. The method of claim 7, wherein said compound is 3-(3,5-dichlorophenyl)-5-iodo-5-methyl-oxazolidine-2,4-dione.

* * * * *